(12) United States Patent
Imamura et al.

(10) Patent No.: US 9,186,124 B2
(45) Date of Patent: Nov. 17, 2015

(54) ULTRASONIC DIAGNOSTIC APPARATUS, ULTRASONIC IMAGE PROCESSING APPARATUS, AND ULTRASONIC IMAGE PROCESSING METHOD

(75) Inventors: Tomohisa Imamura, Nasushiobara (JP); Koichiro Kurita, Nasushiobara (JP); Fumiyasu Sakaguchi, Otawara (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 1141 days.

(21) Appl. No.: 12/337,824

(22) Filed: Dec. 18, 2008

(65) Prior Publication Data
US 2009/0171206 A1 Jul. 2, 2009

(30) Foreign Application Priority Data
Dec. 26, 2007 (JP) .................... 2007-335337

(51) Int. Cl.
*A61B 8/08* (2006.01)
(52) U.S. Cl.
CPC ..................... *A61B 8/08* (2013.01)

(58) Field of Classification Search
USPC ........................ 600/407, 437–475
See application file for complete search history.

(56) References Cited

U.S. PATENT DOCUMENTS

| | | | |
|---|---|---|---|
| 6,475,149 B1 * | 11/2002 | Sumanaweera | 600/441 |
| 6,901,281 B2 * | 5/2005 | Bjornerud et al. | 600/420 |
| 2003/0114756 A1 | 6/2003 | Li | |
| 2004/0225218 A1 * | 11/2004 | Guracar et al. | 600/443 |
| 2007/0055161 A1 * | 3/2007 | Garg et al. | 600/458 |

FOREIGN PATENT DOCUMENTS

CN 1625217 A 6/2005

* cited by examiner

*Primary Examiner* — Mark Remaly
(74) *Attorney, Agent, or Firm* — Oblon, McClelland, Maier & Neustadt, L.L.P.

(57) ABSTRACT

A peripheral region is detected by using original image data acquired by ultrasound scan. Blend processing is executed in the peripheral region such that a rate of a smoothed image increases and a rate of an original image decreases as a distance from a blood flow region increases.

26 Claims, 10 Drawing Sheets

OFF

ON

NORMAL FLOW MAKES
THE PERIPHERY SMOOTH

ABNORMAL BLOOD FLOW
WHOSE SPEED IS HIGH
REDUCES INFLUENCE OF
BLUR AS MUCH AS POSSIBLE

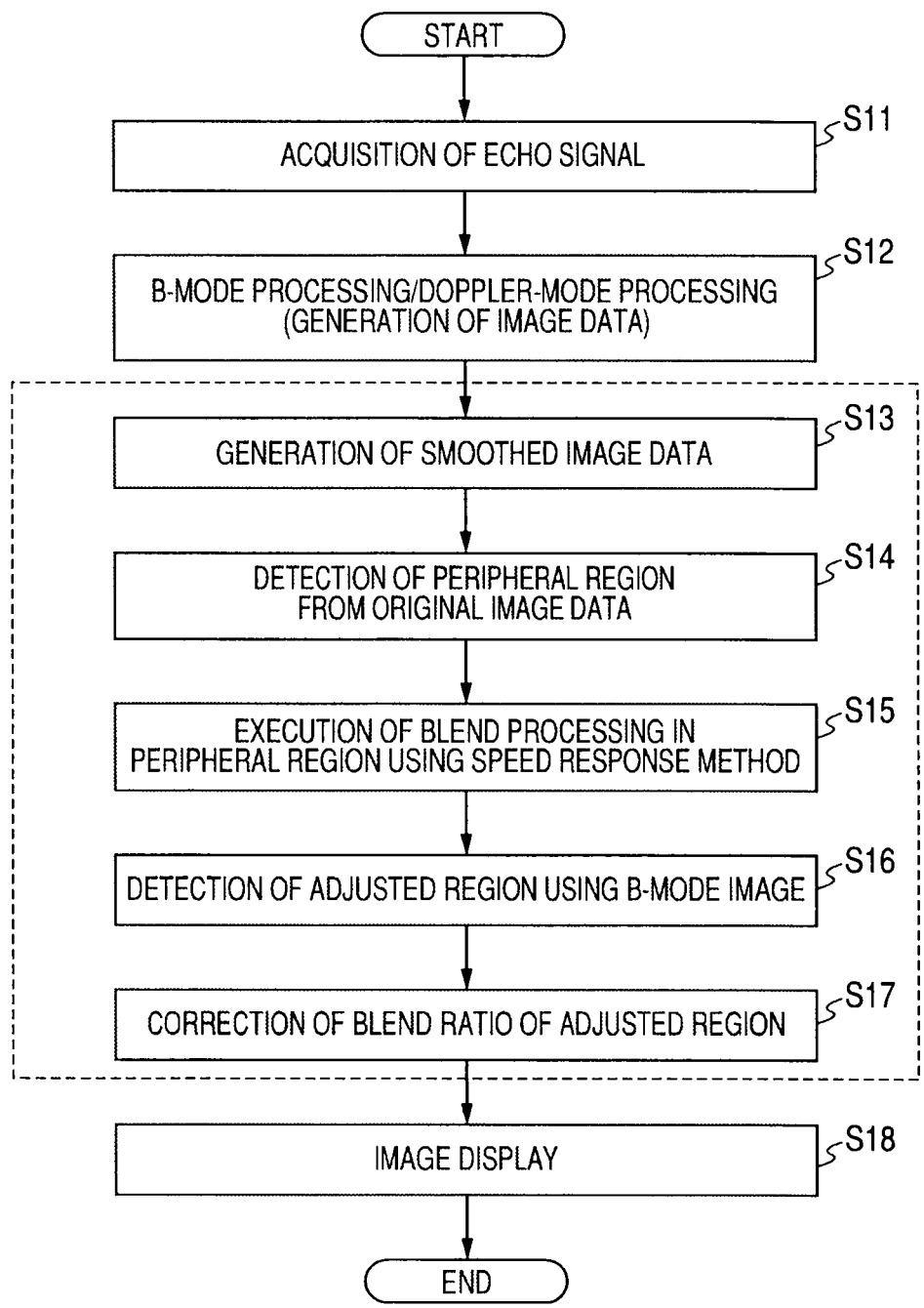

BINARIZATION

ULTRASONIC DIAGNOSTIC APPARATUS, ULTRASONIC IMAGE PROCESSING APPARATUS, AND ULTRASONIC IMAGE PROCESSING METHOD

CROSS-REFERENCE TO RELATED APPLICATIONS

This application is based upon and claims the benefit of priority from prior Japanese Patent Application No. 2007-335337, filed Dec. 26, 2007, the entire contents of which are incorporated herein by reference.

BACKGROUND OF THE INVENTION

1. Field of the Invention

The present invention relates to an ultrasonic diagnostic apparatus, an ultrasonic image processing apparatus, and an ultrasonic image processing method of performing filtering processing for reducing only a noise component without changing the brightness of a signal component from a tissue and the like.

2. Description of the Related Art

The ultrasonic diagnosis makes it possible that the pulsation of the heart or the movement of an embryo is displayed in real time by a simple operation of bringing an ultrasonic probe into contact with a body surface. In addition, since the ultrasonic diagnosis is very safe, the test may be repeatedly performed. In addition, the system size is small compared with other diagnostic apparatuses, such as an X ray, a CT, and an MRI, and a bedside test can also be easily performed. For this reason, it can be said that the ultrasonic diagnosis is an easy diagnostic method. An ultrasonic diagnostic apparatus used in the ultrasonic diagnosis changes in various ways with the type of a function that the apparatus has. As a small ultrasonic diagnostic apparatus, an ultrasonic diagnostic apparatus that is small enough to be carried with one hand is being developed. In addition, since the ultrasonic diagnosis does not cause radioactive exposure unlike the X ray, the ultrasonic diagnosis may also be used in an obstetric treatment, a remote medical treatment, and the like.

However, when performing diagnostic imaging of a circulatory organ in a color Doppler mode using such an ultrasonic diagnostic apparatus, a drawing efficiency may deteriorate, for example, due to ruggedness of the boundary between the inside of a heart chamber and a heart wall or blackening in the normal flow. In this case, it is common to reduce such a problem by performing predetermined smoothing processing.

However, when reducing the ruggedness of the boundary between the inside of the heart chamber and the heart wall or blackening in the normal flow using a smoothing processing method, information which is effective for the diagnosis, such as a blood flow, may also be blurred.

BRIEF SUMMARY OF THE INVENTION

In view of the above, it is an object of the present invention to provide an ultrasonic diagnostic apparatus, an ultrasonic image processing apparatus, and an ultrasonic image processing method capable of reducing the ruggedness of the boundary between the inside of a heart chamber and a heart wall or blackening in the normal flow while suppressing blurring of an ultrasonic image acquired in a color Doppler mode.

According to an aspect of the present invention, there is provided an ultrasonic diagnostic apparatus including: a data generating unit that generates first ultrasonic image data by executing transmission and reception of an ultrasonic wave with respect to a predetermined region of a tested body in a Doppler mode; a detection unit that detects a boundary region between a blood flow region and a tissue region and a peripheral region, which is a region in the neighborhood, by using the first ultrasonic image data; and a correction unit that executes image correction processing at each position of the peripheral region of the first ultrasonic image data by blending the first ultrasonic image data and second ultrasonic image data, which is obtained by executing smoothing processing on the first ultrasonic image data, in a predetermined ratio.

According to another aspect of the present invention, there is provided an ultrasonic image processing apparatus including: a detection unit that detects a boundary region between a blood flow region and a tissue region and a peripheral region, which is a region in the neighborhood, by using first ultrasonic image data acquired by executing transmission and reception of an ultrasonic wave with respect to a predetermined region of a tested body in a Doppler mode; and a correction unit that executes image correction processing at each position of the peripheral region of the first ultrasonic image data by blending the first ultrasonic image data and second ultrasonic image data, which is obtained by executing smoothing processing on the first ultrasonic image data, in a predetermined ratio.

According to yet another aspect of the present invention, there is provided an ultrasonic image processing method including: detecting a boundary region between a blood flow region and a tissue region and a peripheral region, which is a region in the neighborhood, by using first ultrasonic image data acquired by executing transmission and reception of an ultrasonic wave with respect to a predetermined region of a tested body in a Doppler mode; and executing image correction processing at each position of the peripheral region of the first ultrasonic image data by blending the first ultrasonic image data and second ultrasonic image data, which is obtained by executing smoothing processing on the first ultrasonic image data, in a predetermined ratio.

BRIEF DESCRIPTION OF THE SEVERAL VIEWS OF THE DRAWING

FIG. 12 is a flow chart illustrating the flow of tissue response type adjustment processing according to a third embodiment.

DETAILED DESCRIPTION OF THE INVENTION

Figure 1:
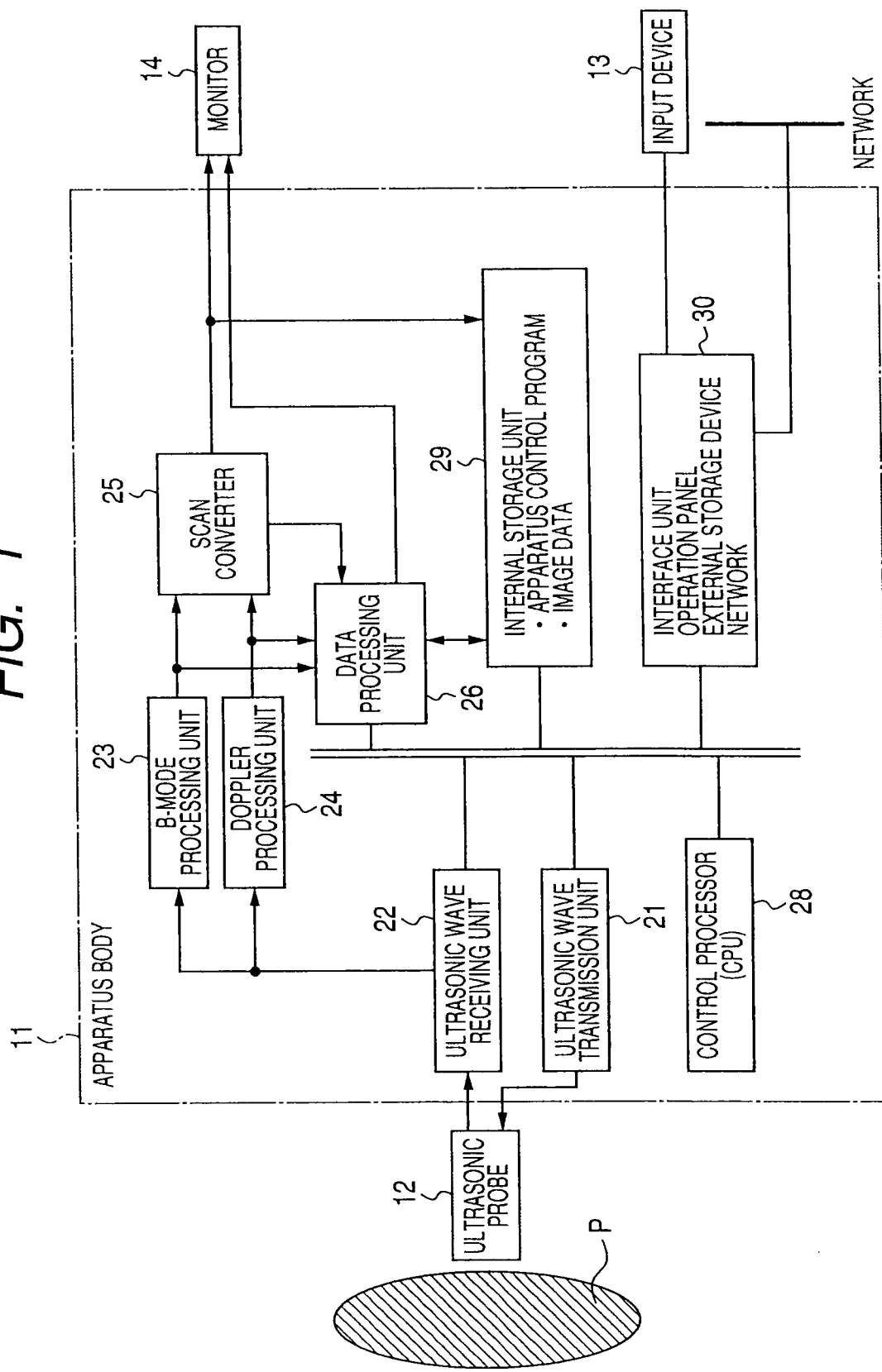
FIG. 1 is a block diagram illustrating the configuration of an ultrasonic diagnostic apparatus according to a first embodiment of the present invention.

Hereinafter, first to third embodiments of the present invention will be described with reference to the accompanying drawings. Moreover, in the following description, components having approximately the same function and configuration are denoted by the same reference numeral, and a repeated explanation thereof will only be made as needed.

(First Embodiment)

FIG. 1 is a block diagram illustrating the configuration of an ultrasonic diagnostic apparatus 1 according to the present embodiment. As shown in the drawing, the ultrasonic diagnostic apparatus 1 includes an ultrasonic probe 12, an input device 13, a monitor 14, an ultrasonic wave transmission unit 21, an ultrasonic wave receiving unit 22, a B-mode processing unit 23, a Doppler processing unit 24, a scan converter 25, a data processing unit 26, a control processor (CPU) 28, an internal storage unit 29, and an interface unit 30. Hereinafter, functions of the constituent components will be described.

The ultrasonic probe 12 generates an ultrasonic wave on the basis of a driving signal from the ultrasonic wave transmission unit 21 and has a plurality of piezoelectric vibrators that convert a reflected wave from a tested body into an electric signal, a matching layer provided in the piezoelectric vibrators, a backing material that prevents propagation of a ultrasonic wave rearward from the piezoelectric vibrators, and the like. When ultrasonic waves are transmitted from the ultrasonic probe 12 to a tested body P, the transmitted ultrasonic waves are sequentially reflected on a discontinuous surface of acoustic impedances of body tissues and are then received as an echo signal by the ultrasonic probe 12. The amplitude of the echo signal depends on a difference of the acoustic impedances on the discontinuous surfaces on which the ultrasonic waves are reflected. In addition, an echo when transmitted ultrasonic pulses are reflected from surfaces of a moving blood flow, a heart wall, and the like receives frequency shift depending on a speed component of a moving body in the ultrasonic wave transmission direction by the Doppler effect.

The input device 13 is connected to an apparatus body 11 and has various switches, buttons, a track ball 13s, a mouse 13c, a keyboard 13d, and the like used to perform various kinds of instructions from an operator, an instruction for setting a condition or a region of interest (ROI), an instruction for setting various image quality conditions, and the like on the apparatus body 11. For example, when an operator operates a stop button or a FREEZE button of the input device 13, transmission and reception of an ultrasonic wave are stopped and the ultrasonic diagnostic apparatus is temporarily stopped.

The monitor 14 displays morphological information or blood flow information in the living body, as an image, on the basis of a video signal from the scan converter 25.

The ultrasonic wave transmission unit 21 has a trigger generating circuit, a delay circuit, and a pulse circuit which are not shown. The pulse circuit repeatedly generates a rate pulse for forming a transmitted ultrasonic wave at a predetermined rate frequency fr Hz (period; 1/fr second). In addition, the delay circuit makes ultrasonic waves converge in the beam shape for every channel and gives a delay time, which is required for determining the transmission directivity, to each rate pulse. The trigger generating circuit applies a driving pulse to the probe 12 at a timing based on the rate pulse.

The ultrasonic wave receiving unit 22 has an amplifying circuit, an A/D converter, an adder, and the like which are not shown. The amplifying circuit amplifies an echo signal received through the probe 12 for every channel. The A/D converter gives a delay time, which is required to determine the receiving directivity, to the amplified echo signal, and then the adder performs adding processing. By this addition, a reflected component from a direction according to the receiving directivity of echo signals is emphasized and overall beams in ultrasonic transmission and reception are formed by the receiving directivity and the transmission directivity.

The B-mode processing unit 23 receives an echo signal from the ultrasonic wave receiving unit 22, performs logarithmic amplification and envelope detection processing, and generates data in which the signal strength is expressed as brightness. This data is transmitted to the scan converter 25 and is displayed on the monitor 14 as a B-mode image which expresses the strength of a reflected wave with the brightness.

The Doppler processing unit 24 makes a frequency analysis of speed information from the echo signal received from the ultrasonic wave receiving unit 22, extracts a blood flow or a tissue and a contrast echo component due to the Doppler effect, and calculates blood flow information, such as an average speed, diffusion, and power, with respect to multiple points. The acquired blood flow information is transmitted to the scan converter 25 to be color-displayed on the monitor 14 as an average speed image, a diffusion image, a power image, and a combination image thereof.

The scan converter 25 mixes a scanning line signal row of ultrasonic scan with character information, scale, and the like of various parameters of data received from the B-mode processing unit 23, the Doppler processing unit 24, and the data processing unit 26, converts the result into a scanning line signal row in a typical video format represented by a television, and generates an ultrasonic diagnostic image as a display image. The scan converter 25 has a storage memory in which image data is stored, for example, so that an operator can call an image recorded in a test after diagnosis. In addition, data before being input to the scan converter 25 is a group of amplitude values or brightness values for every spatial position and is called 'raw data'.

The data processing unit 26 executes processing (peripheral region smoothing processing) according to a peripheral region smoothing function, which will be described later, on the basis of the control from the control processor 28 using raw data before scan conversion or image data after scan conversion.

The control processor 28 has a function as an information processing device (computer), and is a control unit that controls an operation of the ultrasonic diagnostic apparatus body. The control processor 28 reads from the internal storage unit 29 a control program for executing image generation, image display, and the like, loads the control program onto the memory that the control processor 28 has, and executes calculation, control, and the like on various kinds of processing.

The internal storage unit 29 stores a control program for executing predetermined scan sequence, image generation, and display processing, diagnostic information (for example, a patient ID and doctor's opinion), a diagnostic protocol, transmission and reception conditions, a body mark generating program, and other data groups. The data in the internal storage unit 29 may also be transmitted to an external peripheral device through the interface unit 30.

The interface unit 30 is an interface related to the input device 13, a network, and a new external storage device (not shown). Data or an analysis result of an ultrasonic image obtained by the apparatus may be transmitted to other apparatuses through the network by the interface unit 30.

(Peripheral Region Smoothing Function)

Next, a peripheral region smoothing function of the ultrasonic diagnostic apparatus 1 will be described. This function is to smooth a peripheral region by performing correction for blending a smoothed image in a boundary between a blood flow region (for example, inside of a heart chamber) and a tissue region (for example, a heart wall) in an ultrasonic image acquired in a color Doppler mode and/or a peripheral region (hereinafter, simply referred to as a 'peripheral region'), which is a region in the neighborhood, in an ultrasonic image. This function makes it possible to reduce the blur or ruggedness in a peripheral region and to improve the visibility of an ultrasonic image.

Moreover, in the present embodiment, for the purpose of specific explanation, a case where the peripheral region smoothing function is applied to image data, which is the data after scan conversion, will be exemplified. However, the function may also be applied to raw data which is data before scan conversion regardless of a data format.

In addition, in the present embodiment, a case of realizing the peripheral region smoothing function by the ultrasonic diagnostic apparatus 1 will be described as an example. However, a function of imaging an ultrasonic image is not essential in realizing the peripheral region smoothing function. For example, it may be possible to install a dedicated program in an ultrasonic image processing apparatus, such as a medical workstation, and to execute the peripheral region smoothing function on ultrasonic image data or ultrasonic raw data acquired beforehand.

Figure 2:
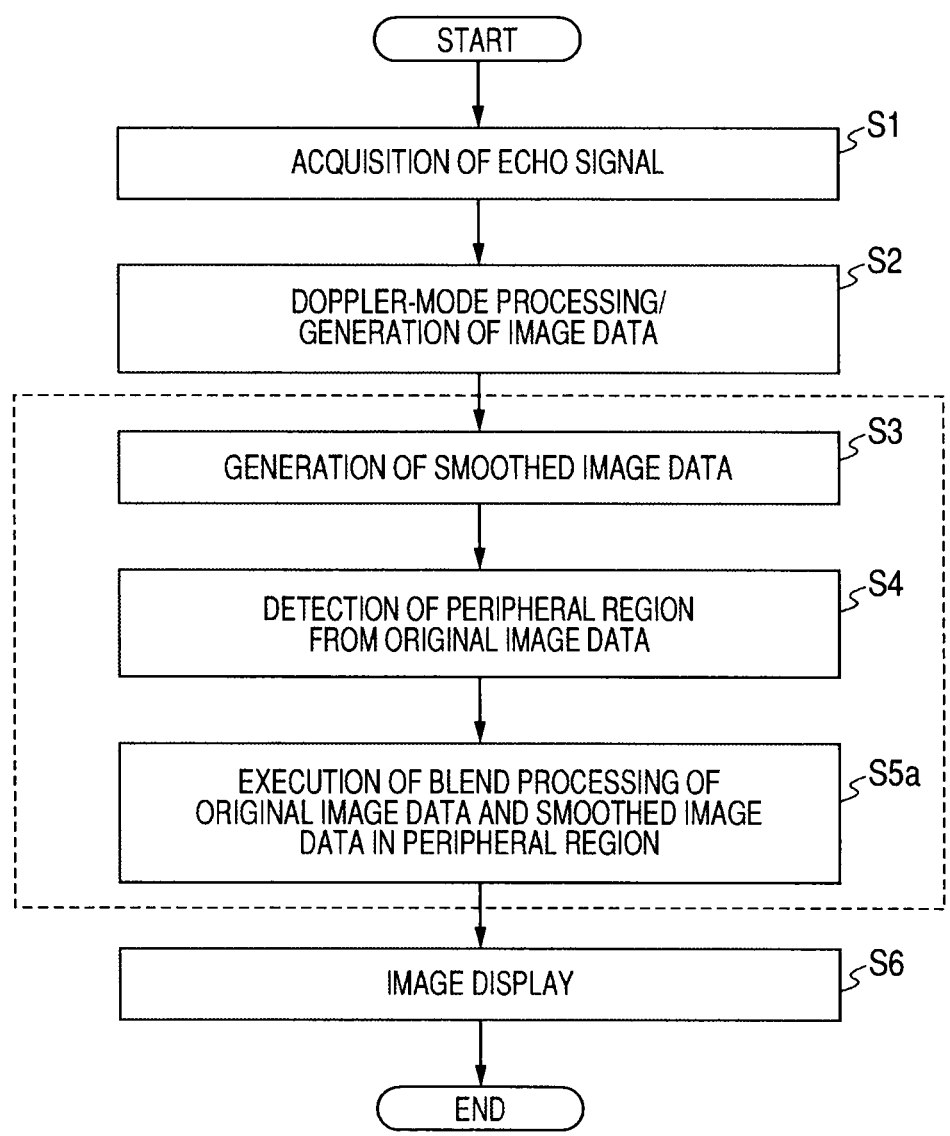
FIG. 2 is a flow chart illustrating the flow of peripheral region smoothing processing.

FIG. 2 is a flow chart illustrating the flow of peripheral region smoothing processing. Hereinafter, details of the processing in each step will be described. In this flow chart, steps S3 to S6 correspond to the peripheral region smoothing processing.

[Ultrasonic Scan (Acquisition of an Echo Signal): Step S1]

First, the control processor 28 executes Doppler-mode imaging according to a predetermined scan sequence and acquires an echo signal (step S1).

[Doppler-Mode Processing (Generation of Image Data): Step S2]

Then, the Doppler processing unit 24 makes a frequency analysis of speed information from the echo signal received from the ultrasonic wave receiving unit 22, extracts a blood flow or a tissue and a contrast echo component due to the Doppler effect, calculates blood flow information, such as an average speed, dispersion, and power, with respect to multiple points, and generates raw data on the Doppler image. The scan converter 25 generates image data using the raw data received from the Doppler processing unit 24 (step S2).

[Generation of Smoothed Image Data: Step S3]

Then, the data processing unit 26 generates smoothed image data using a predetermined method (step S3). Here, the smoothed image data is generated by using original image data (that is, data acquired in step S2) in order to lower the resolution compared with an original image.

This smoothed image data is used to remove the ruggedness of the peripheral region and the like by recognizing a signal region macroscopically. Although the generation method is not limited, typical examples thereof are as follows.

Figure 3:
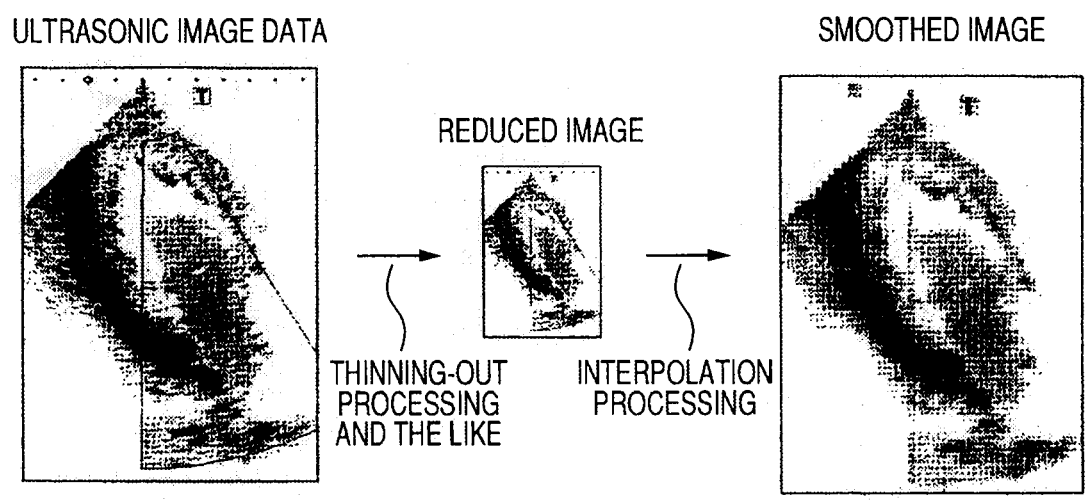
FIG. 3 is a view illustrating the generation of smoothed image data.

That is, first, the data processing unit 26 generates a reduced image of a corresponding image using the ultrasonic image data acquired in step S2, as shown in FIG. 3. On the reduced image, mapping processing of setting small regions (for example, small regions of 3×3=9 pixels) with a predetermined size on image data, calculating an average value of the small regions using a predetermined window function, and setting the average value as a pixel value of a predetermined position of the reduced image is performed. Then, the middle of the small region is moved, for example, to an adjacent pixel to perform the same mapping processing. By executing such mapping processing on all pixels on the image data, the reduced image can be generated. In addition, as another method, the reduced image may also be generated by thinning out pixels in a predetermined rate (for example, 1/2 or 1/3), for example.

Then, smoothed image data can be generated by interpolating the obtained reduced image using a predetermined technique (for example, two-dimensional Spline interpolation) in order to generate an image with the original size.

[Detection of a Peripheral Region from Original Image Data: Step S4]

Then, the data processing unit 26 detects a peripheral region using the original image data (step S4).

Figure 4:
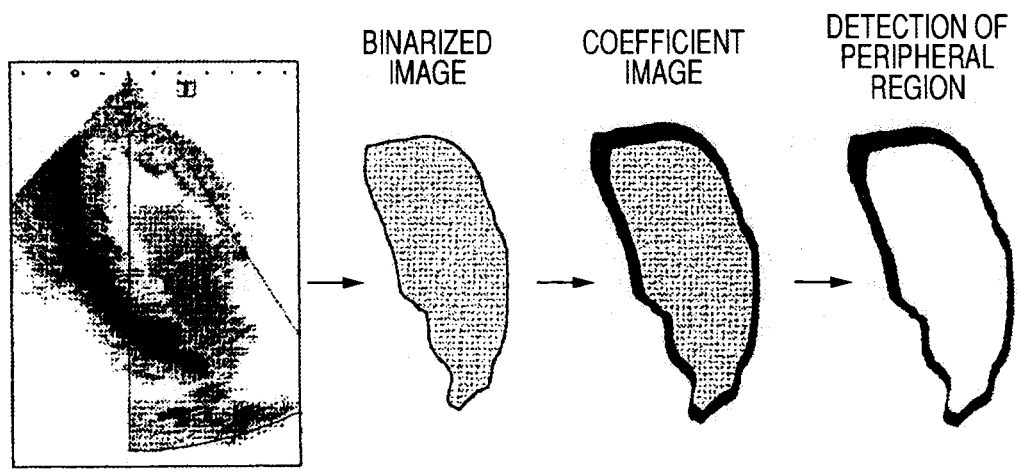
FIG. 4 is a view illustrating processing for detecting a peripheral region from original image data.

That is, first, the data processing unit 26 acquires a binarized image by executing binarization processing on the ultrasonic image data acquired in step S2, as shown in FIG. 4.

Then, the data processing unit 26 generates a coefficient image by executing filtering processing on the obtained binarized image a predetermined number of times. For example, mapping processing of setting a predetermined number of small regions (for example, small regions of 3×3=9 pixels) on image data, calculating an average value of the small regions using a predetermined window function, and setting the average value as a pixel value of a middle position of the reduced image as a coefficient is performed. Then, the middle of the small region is moved to an adjacent pixel, for example, to perform the same mapping processing. By executing such mapping processing on all pixels on the image data, the coefficient image shown in FIG. 4 can be generated.

Then, the data processing unit 26 detects the peripheral region as shown in FIG. 4 by determining a pixel having a value of 0 or more and less than 1 as a peripheral region and a pixel having a value of 1 as a non-peripheral region in the coefficient image.

[Execution of Blend Processing in a Peripheral Region: Step S5*a*]

Then, the data processing unit 26 executes blend processing in the peripheral region according to a predetermined blend ratio (step S5*a*). That is, the data processing unit 26 raises the blend rate (weighting factor) of an original image and lowers the blend rate (weighting factor) of a smoothed image in a peripheral region near a side of a blood flow region (heart chamber side), for example, according to the blend ratio shown in FIG. 5. On the other hand, the data processing unit 26 lowers the blend rate of the original image and raises the blend rate of the smoothed image in the peripheral region as the distance from the blood flow region increases.

Figure 5:
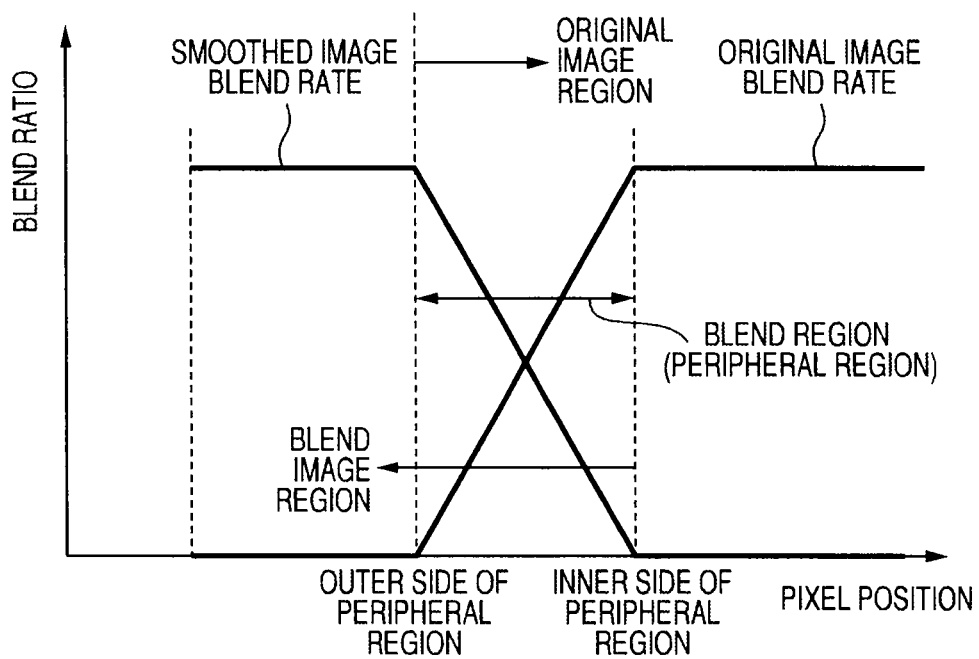
FIG. 5 is a view illustrating an example of the blend ratio used in blend processing in a peripheral region.

Moreover, when observing the Doppler image, a high-resolution image is requested for the blood flow region (inner side of the peripheral region). Accordingly, for example, as shown in FIG. 5, the rate of the smoothed image is set to 0 and all information on the original image is used. On the other hand, for an outer side of the peripheral region, an image with particularly high resolution is rarely requested. Accordingly, for example, as shown in FIG. 5, the rate of the original image is set to 0 and all information on the smoothed image is used.

In addition, the blend ratio shown in FIG. 5 is only illustrative. That is, any blend ratio may be adopted as long as the blend rate of the original image decreases and the blend rate of the smoothed image increases as the distance from the blood flow region increases.

[Display of an Ultrasonic Image: Step S6]

Then, the monitor 14 displays an ultrasonic image, in which the contrast between an effective diagnostic component and an ineffective diagnostic component is emphasized, in a predetermined format on the basis of a video signal from the data processing unit 26 (step S6).

Figure 6A:
FIG. 6A is a view illustrating a known ultrasonic image on which peripheral region smoothing processing is not executed.
Figure 6B:
FIG. 6B is a view illustrating an ultrasonic image on which the peripheral region smoothing processing was executed.

FIG. 6A is a view illustrating a known ultrasonic image on which the peripheral region smoothing processing is not executed. FIG. 6B is a view illustrating an ultrasonic image on which the peripheral region smoothing processing was executed. Comparing FIGS. 6A and 6B, it can be seen that in the case of FIG. 6B, the ruggedness of a peripheral region is reduced by the peripheral region smoothing processing and the blur caused by the peripheral region smoothing processing does not occur either, compared with FIG. 6A.

(Data Amount Reduction Function)

Next, a data amount reduction function of the ultrasonic diagnostic apparatus will be described. This function is to rotate ultrasonic image data for every frame and to reduce the total amount of data read from a memory. By executing processing (data amount reduction processing) based on the function, for example, before peripheral region smoothing processing, the throughput until the ultrasonic image is displayed can be improved and the ultrasonic image display can be realized in real time.

Figure 7A:
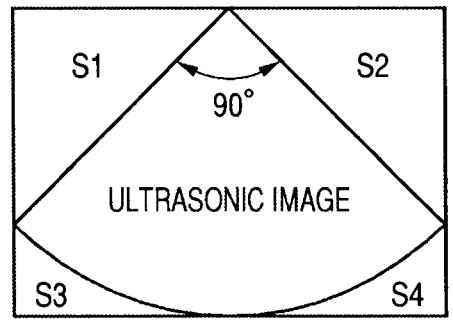
FIGS. 7A, 7B, and 7C are views illustrating an example for explaining data amount reduction processing.
Figure 7B:
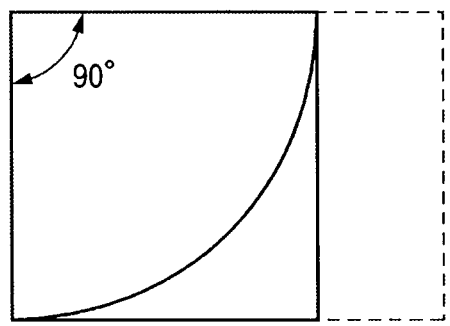
Figure 7C:
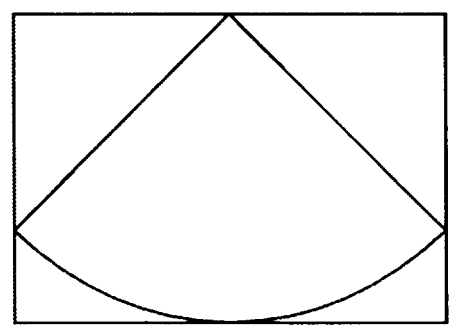

FIGS. 7A, 7B, and 7C are views illustrating an example for explaining the data amount reduction processing. When ultrasound scan based on sector scan is performed, image data after scan conversion has a fan shape shown in FIG. 7A. When writing/reading the image data with the fan shape into a memory, the image data is written and read into a rectangular region shown in FIG. 7A in a known apparatus. For this reason, the writing/reading was also performed in unnecessary regions, such as S1, S2, and S3, other than ultrasonic image data.

In this data amount reduction processing, for example, the obtained ultrasonic image data is rotated on the basis of the shape or size of an ultrasonic scan region such that the area of a rectangular region including the image data becomes minimal as shown in FIG. 7B, thereby minimizing a memory region used to write/read the image data. The above-described peripheral region smoothing processing is executed on the image data written in the memory region minimized as described above. Then, the image data is rotated to return to the original direction, as shown in FIG. 7C. Thus, the throughput until the ultrasonic image is displayed can be improved, and the ultrasonic image display can be realized in real time.

Figure 8A:
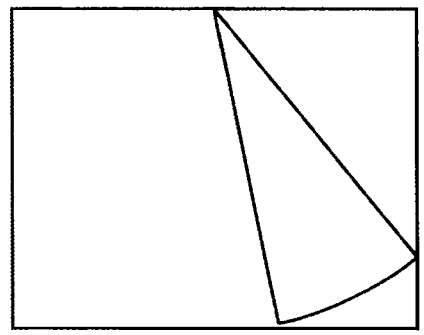
FIGS. 8A, 8B, and 8C are views illustrating another example for explaining the data amount reduction processing.
Figure 8B:
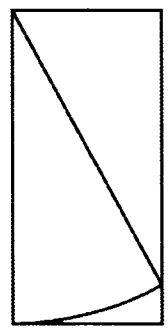
Figure 8C:
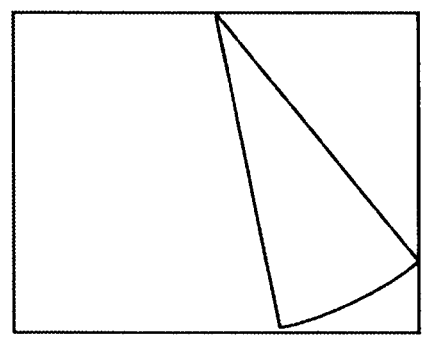

Furthermore, also when an ultrasonic scan region is inclined with respect to an ultrasonic wave irradiation surface as shown in FIG. 8A, for example, image data is rotated such that the area of a rectangular region including the image data becomes minimal as shown in FIG. 8B, thereby minimizing a memory region used to write/read the image data. Then, the image data is rotated to return to the original direction, as shown in FIG. 8C. Thus, the throughput until the ultrasonic image is displayed can be improved, and the ultrasonic image display can be realized in real time.

According to the configuration described above, the following effects can be obtained.

In the ultrasonic diagnostic apparatus according to the present embodiment, a peripheral region is detected by using original image data acquired by ultrasonic scan, and blend processing is executed in the peripheral region such that the rate of the original image decreases and the rate of the smoothed image increases as the distance from the blood flow region increases and such that the rate of the original image increases and the rate of the smoothed image decreases as the distance from the blood flow region decreases. Therefore, in an image acquired in the Doppler mode, it is possible to reduce the ruggedness in a peripheral region and its neighborhood while maintaining the image quality of a blood flow region. As a result, the visibility of an ultrasonic image can be improved, which contributes to reducing the load in an observation work in diagnostic imaging and improving the quality of the diagnostic imaging.

Furthermore, in the ultrasonic diagnostic apparatus according to the present embodiment, an ultrasonic image in which original image data is used at the inner side of the peripheral region and smoothed image data is used at the outer side of the peripheral region is generated. Accordingly, an ultrasonic image can be observed with high resolution in a blood flow region inside the peripheral region and in a natural form for human eyes at the outer side of the peripheral region, in the image acquired in the Doppler mode. As a result, the visibility of an ultrasonic image can be improved, which contributes to reducing the load in an observation work in diagnostic imaging and improving the quality of the diagnostic imaging.

Furthermore, in the ultrasonic diagnostic apparatus, when writing image data into a memory, the amount of data to be processed can be reduced by rotating the ultrasonic scan range such that the amount of data written or read becomes minimal. As a result, the throughput until the ultrasonic image is displayed can be improved, and the ultrasonic image display can be realized in real time.

(Second Embodiment)

Next, a second embodiment of the present invention will be described. In the peripheral region smoothing processing described in the first embodiment, for example, some blur may be felt at the end of the peripheral region. The blur at the end of the peripheral region may make worse a drawing efficiency of a small backward component generated near the end, for example.

In order to solve such a problem, an ultrasonic diagnostic apparatus according to the present embodiment has a function (speed response type adjustment function) of adjusting a blend ratio of a smoothed image and an original image according to the speed.

Figure 9:
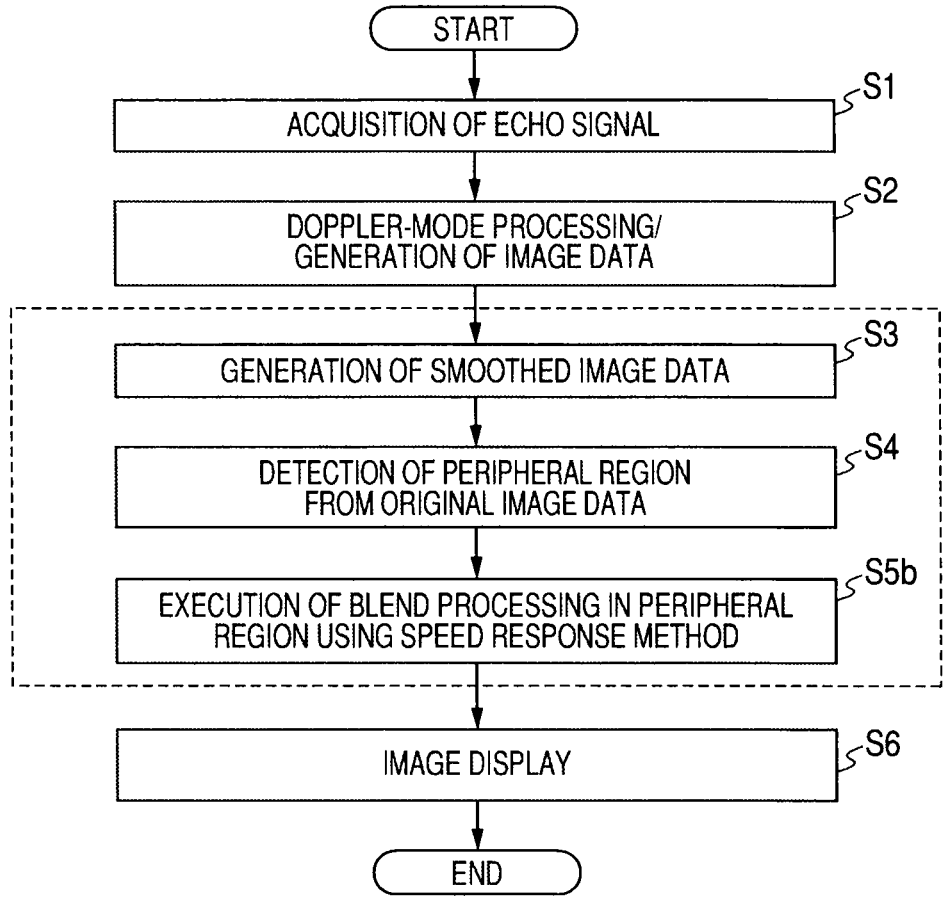
FIG. 9 is a flow chart illustrating the flow of speed response type adjustment processing according to a second embodiment.

FIG. 9 is a flow chart illustrating the flow of processing (speed response type adjustment processing) based on the speed response type adjustment function according to the present embodiment. In addition, steps S1 to S4 are the same as described in the first embodiment.

[Execution of Blend Processing in a Peripheral Region Using a Speed Response Method: Step S5b]

Then, the data processing unit 26 executes blend processing in the peripheral region according to a predetermined blend ratio corresponding to the position and speed in the peripheral region (step S5b).

That is, the data processing unit 26 first determines a blend ratio at each position of a peripheral region according to the blend ratio shown in FIG. 5.

Figure 10:
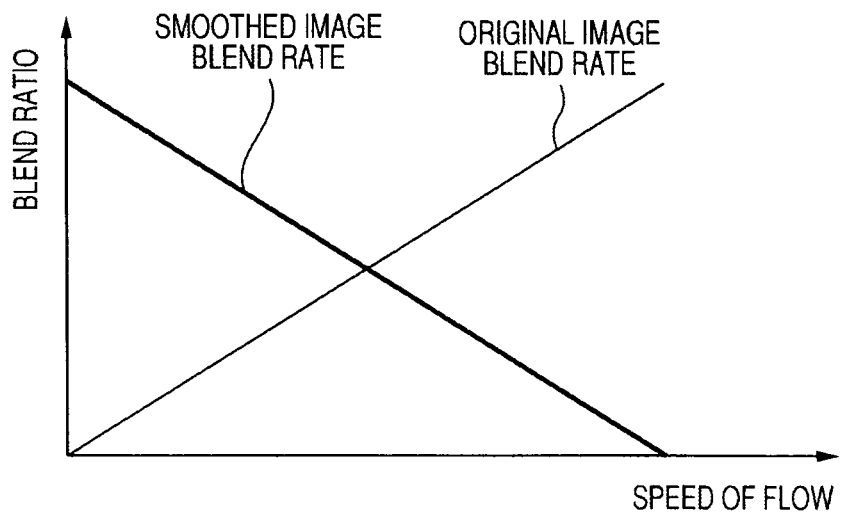
FIG. 10 is a view illustrating an example of a blend ratio used in speed response type adjustment processing.

Then, for example, according to a blend ratio shown in FIG. 10, the data processing unit 26 determines a blend ratio at each position of the peripheral region corresponding to the speed. That is, the data processing unit 26 acquires the speed at each position of the peripheral region on the basis of a Doppler signal, and adjusts the blend ratio at each position according to the correspondence relationship shown in FIG. 10 such that the rate of original image data is raised when the speed is high and the rate of smoothed image data is raised when the speed is low.

In addition, the blend ratio shown in FIG. 10 is only illustrative. That is, any blend ratio may be adopted as long as the blend ratio is to raise the rate of original image data when the speed is high and raise the rate of a smoothed image when the speed is low in the peripheral region.

[Display of an Ultrasonic Image: Step S6]

Then, the monitor 14 displays an ultrasonic image, in which the contrast between an effective diagnostic component and an ineffective diagnostic component is emphasized, in a predetermined format on the basis of a video signal from the data processing unit 26 (step S6).

Figure 11A:
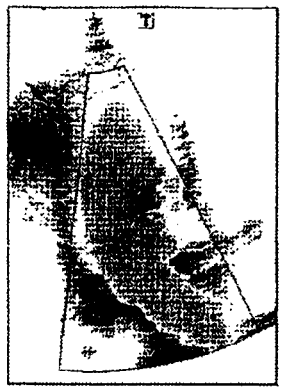
FIG. 11A is a view illustrating a known ultrasonic image on which the speed response type adjustment processing is not executed.
Figure 11B:
FIG. 11B is a view illustrating an ultrasonic image on which the speed response type adjustment processing was executed.

FIG. 11A is a view illustrating an ultrasonic image on which the speed response type adjustment processing is not executed. FIG. 11B is a view illustrating an ultrasonic image on which the speed response type adjustment processing was executed. Comparing FIGS. 11A and 11B, it can be seen that in the case of FIG. 11B, information on an original image is maintained in a region where the speed (speed of flow) is high and a smooth image is obtained in a peripheral region or a normal flow region in the neighborhood by the speed response type adjustment processing, compared with FIG. 11A.

According to the configuration described above, the following effects can be obtained.

In the ultrasonic diagnostic apparatus according to the present embodiment, the blend ratio at each position is adjusted such that the rate of original image data is raised when the speed is high and the rate of a smoothed image is raised when the speed is low. Therefore, even if the peripheral region smoothing processing is executed on an image acquired in the Doppler mode, information on the original image can be maintained in a region where the speed is high and an image made smooth can be generated in a peripheral region or a normal flow region in the neighborhood.

(Third Embodiment)

Next, a third embodiment of the present invention will be described.

In general, even a normal blood flow may be fast near the myocardium. When the speed response type adjustment processing described in the second embodiment is executed in such a situation, an original image is preferentially displayed for the normal blood flow near the myocardium. As a result, the ruggedness of a peripheral region or its neighborhood may not be appropriately reduced.

In order to solve such a problem, the ultrasonic diagnostic apparatus according to the present embodiment has a function (tissue response type adjustment function) of lowering the blend rate of the original image and raising the blend rate of the smoothed image in a color region near a high-brightness region (that is, a region corresponding to the myocardium) on a B-mode image by using the image (B-mode image) acquired by the B-mode imaging.

FIG. 12 is a flow chart illustrating the flow of processing (tissue response type adjustment processing) based on the tissue response type adjustment function according to the present embodiment. Hereinafter, details of the processing in each step will be described.

[Ultrasonic Scan (Acquisition of an Echo Signal): Step S11]

First, the control processor 28 executes B-mode imaging and Doppler-mode imaging according to a predetermined scan sequence and acquires an echo signal (step S11).

[Doppler-Mode Processing (Generation of Image Data): Step S12]

Then, the B-mode processing unit 23 performs logarithmic amplification and envelope detection processing on the echo signal acquired by the B-mode imaging and generates raw data on the B-mode image. Then, the Doppler processing unit 24 makes a frequency analysis of speed information from the echo signal acquired by the Doppler-mode imaging, extracts a blood flow or a tissue and a contrast echo component due to the Doppler effect, calculates blood flow information, such as an average speed, dispersion, and power, with respect to multiple points, and generates raw data on the Doppler image. The scan converter 25 generates B-mode image data and Doppler-mode image data using the raw data on the B-mode image and the raw data on the Doppler-mode image (step S12).

[Generation of Smoothed Image Data: Step S13]

Then, the data processing unit 26 generates smoothed image data using the Doppler-mode image data (original image data) acquired in step S12 (step S13). Processing in this step is substantially the same as that in step S3 described earlier.

[Detection of a Peripheral Region from Original Image Data: Step S14]

Then, the data processing unit 26 detects a peripheral region using the original image data (step S14). Processing in this step is substantially the same as that in step S4 described earlier.

[Execution of Blend Processing in a Peripheral Region Using a Speed Response Method: Step S15]

Then, the data processing unit 26 executes blend processing in the peripheral region according to a predetermined blend ratio corresponding to the position and speed in the peripheral region (step S15). Processing in this step is substantially the same as that in step S5b described earlier.

[Detection of an Adjusted Region Using a B-Mode Image: Step S16]

Figure 13A:
FIGS. 13A, 13B, and 13C are views illustrating processing of detecting an adjusted region using a B-mode image.
Figure 13B:
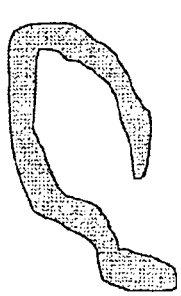

The data processing unit 26 detects an adjusted region using the B-mode image data (step S16). That is, the data processing unit 26 first executes binarization processing on a B-mode image shown in FIG. 13A and acquires a binarized image shown in FIG. 13B.

Figure 13C:
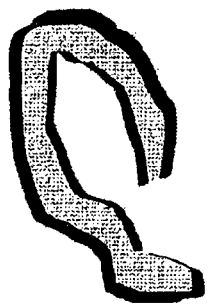

Then, the data processing unit 26 generates a coefficient image by executing filtering processing on the obtained binarized image a predetermined number of times. For example, mapping processing of setting a predetermined number of small regions (for example, small regions of 3×3=9 pixels) on image data, calculating an average value of the small regions using a predetermined window function, and setting a pixel value of a middle position of a reduced image using the average value as a coefficient is performed. Then, the middle of the small region is moved, for example, to an adjacent pixel to perform the same mapping processing. By executing such mapping processing on all pixels on the image data, a coefficient image shown in FIG. 13C can be generated.

Then, the data processing unit 26 detects a region, which has a pixel whose coefficient is 0 or more and less than 1, as an adjusted region in the coefficient image.

[Adjustment of a Blend Ratio in an Adjusted Region: Step S17]

Then, the data processing unit 26 adjusts a blend ratio in an adjusted region (step S17). That is, the data processing unit 26 determines that a pixel with a high coefficient is close to a high-brightness region of the B-mode image, in a region corresponding to the adjusted region on the Doppler image, and makes an adjustment such that the blend rate of the smoothed image is raised. On the other hand, the data processing unit 26 determines that a pixel with a low coefficient is far from the high-brightness region of the B-mode image and makes an adjustment such that the blend rate of the original image is raised.

[Display of an Ultrasonic Image: Step S18]

Then, the monitor 14 displays an ultrasonic image in a predetermined format on the basis of a video signal from the data processing unit 26 (step S18).

According to the configuration described above, the following effects can be obtained.

The ultrasonic diagnostic apparatus according to the present embodiment detects an adjusted region which is a region close to the high-brightness region on the B-mode image, determines a pixel with a high coefficient to be close to the high-brightness region on the B-mode image in the adjusted region, and makes an adjustment such that the blend rate of the smoothed image is raised. On the other hand, the data processing unit 26 determines that a pixel with a low coefficient is far from the high-brightness region of the B-mode image and makes an adjustment such that the blend rate of the original image is raised. As a result, even if a normal blood flow which is fast occurs near the myocardium, the ruggedness of the peripheral region can be reduced and, for example, the blood flowing backward, which is not generated near the myocardium, can be visualized with a small influence of blur.

In addition, the present invention is not limited to the embodiment described above but may be embodied in practice by modifying constituent components without departing from the scope and spirit of the present invention. For example, specific modifications include the following examples.

(1) Each of the functions in the present embodiment may be realized by installing a program, which is used to execute corresponding processing, in a computer, such as a workstation, and then loading the program onto a memory. In this case, a program capable of causing a computer to execute a corresponding technique may be distributed in a state where the program is stored in a recording medium, such as a magnetic disk (for example, a floppy (registered trademark) disk or a hard disk), an optical disk (for example, a CD-ROM or a DVD), and a semiconductor memory.

(2) In the above embodiment, the case of executing the peripheral region smoothing processing on two-dimensional ultrasonic image data has been described as an example. However, the peripheral region smoothing processing is not limited to the two-dimensional image data. For example, the peripheral region smoothing processing may also be executed on three-dimensional image data by dividing the three-dimensional image data into two-dimensional image data items and executing the peripheral region smoothing processing on each of the two-dimensional image data items. In addition, the peripheral region smoothing processing may also be realized by setting a small region as regions of 3×3×3=27 pixels, generating blurred image volume data, setting a small region (for example, a small region of 3×3=9 pixels) with a predetermined size on the image data, and performing the same processing in the unit of volume data in step S3, for example.

(3) If a predetermined maximum brightness value does not change more than a predetermined designated brightness value in observing an ultrasonic image, it is general that a visual change is not felt even if image data is updated. Accordingly, in the above embodiment, in the case when corresponding pixel values between adjacent frames, for example, before and after peripheral region smoothing processing are compared with each other and the difference is smaller than a predetermined value for all pixels, image data of a new frame may not be transmitted for subsequent processing. According to such configuration, since the amount of data to be processed can be reduced, an image can be provided in real time.

In addition, various kinds of inventions may be realized by proper combination of the plurality of constituent components disclosed in the embodiments described above. For example, some constituent components may be eliminated from all components shown in the above embodiment. Moreover, constituent components in different embodiments may be appropriately combined.

What is claimed is:

1. An ultrasonic diagnostic apparatus comprising:
a probe that transmits ultrasonic waves to a heart and receives reflected waves from the heart;
an image generating processor that generates an original Doppler image corresponding to a scan region including a blood flow region and a tissue region of the heart based on the reflected waves received by the probe, wherein the original Doppler image represents blood flow in the heart;
a detection processor that detects a predetermined region by image processing for an ultrasonic image, wherein a position of the predetermined region depends on a position of a boundary between the blood flow region and the tissue region; and
a correction processor that (a) generates a smoothed Doppler image by smoothing at least the predetermined region of the original Doppler image, (b) generates a first weighted image by weighting at least the predetermined region of the original Doppler image with a first weighting factor and generates a second weighted image by weighting at least the predetermined region of the smoothed Doppler image with a second weighting factor, and (c) generates a blended image by blending the first weighted image and the second weighted image.

2. The ultrasonic diagnostic apparatus according to claim 1,
wherein the first weighting factor and the second weighting factor for each image element in the predetermined region depend on a position of the each image element in the predetermined region.

3. The ultrasonic diagnostic apparatus according to claim 1,
wherein the first weighting factor and the second weighting factor for each image element in the predetermined region depend on a speed of a blood flow or a speed of a tissue at the each image element.

4. The ultrasonic diagnostic apparatus according to claim 1,
wherein the correction processor further varies the blending in response to a distance from the tissue region to the predetermined region.

5. The ultrasonic diagnostic apparatus according to claim 1,
wherein the detection processor detects the blood flow region; and
the correction processor further executes image correction processing using only the second weighted image in a region other than the blood flow region.

6. The ultrasonic diagnostic apparatus according to claim 1, further comprising:
a memory; and a writing processor that determines a writing direction of data of the original Doppler image into the memory in response to size and shape of the predetermined region to which an ultrasonic wave is transmitted and that writes the data into the memory according to the determined direction, wherein each of the detection processor and the correction processor executes processing by using the data written into the memory according to the determined direction.

7. The ultrasonic diagnostic apparatus according to claim 1,
wherein the original Doppler image data and ultrasonic image data are three-dimensional image data.

8. The ultrasonic diagnostic apparatus according to claim 1, wherein the predetermined region is a peripheral region of the boundary.

9. The ultrasonic diagnostic apparatus according to claim 1, wherein the second weighting factor depends on the first weighting factor.

10. The ultrasonic diagnostic apparatus according to claim 8, wherein the Doppler image is generated by superimposing blood flow information in the blood flow region on a tissue image.

11. The ultrasonic diagnostic apparatus according to claim 10, wherein the ultrasonic image is the original Doppler image.

12. The ultrasonic diagnostic apparatus according to claim 10, wherein the ultrasonic image is a tissue image.

13. An ultrasonic diagnostic apparatus comprising:
a storage that stores an original Doppler image corresponding to a scan region including a blood flow region and a tissue region of the heart by scanning the scan region with an ultrasonic wave in a Doppler mode, wherein the original Doppler image represents blood flow in the heart;
a detection processor that detects a predetermined region by image processing for an ultrasonic image, wherein a position of the predetermined region depends on a position of a boundary between the blood flow region and the tissue region; and
a correction processor that (a) generates a smoothed Doppler image by smoothing at least the predetermined region of the original Doppler image, (b) generates a first weighted image by weighting at least the predetermined region of the original Doppler image with a first weighting factor and generates a second weighted image by weighting at least the predetermined region of the smoothed Doppler image with a second weighting factor, and (c) generates a blend image by blending the first weighted image and the second weighted image.

14. The ultrasonic diagnostic apparatus according to claim 13,
wherein the first weighting factor and the second weighting factor for each image element in the predetermined region depend on a position of the each image element in the predetermined region.

15. The ultrasonic diagnostic apparatus according to claim 13,
wherein the first weighting factor and the second weighting factor for each image element in the predetermined region depend on a speed of a blood flow or a speed of a tissue at the each image element.

16. The ultrasonic image processing apparatus according to claim 13,
wherein the correction processor further varies the blending in response to a distance from the tissue region to the predetermined region.

17. The ultrasonic image processing apparatus according to claim 13,
wherein the detection processor detects the blood flow region; and
the correction processor further executes image correction processing using only the second weighted image in a region other than the blood flow region.

18. The ultrasonic image processing apparatus according to claim 13, further comprising:
a memory;
a writing processor that determines a writing direction of data of the original Doppler image into the memory in response to size and shape of the predetermined region to which an ultrasonic wave is transmitted and that writes the data into the memory according to the determined direction,
wherein each of the detection processor and the correction processor executes processing by using the data written into the memory according to the determined direction.

19. The ultrasonic image processing apparatus according to claim 13,
wherein the original Doppler image data and ultrasonic image data are three-dimensional image data.

20. An ultrasonic image processing method comprising:
transmitting, by a probe, ultrasonic waves to a heart and receiving reflected waves from the heart;
generating an original Doppler image corresponding to a scan region including a blood flow region and a tissue region of the heart based on the reflected wave received by the probe, wherein the original Doppler image represents blood flow in the heart;
detecting a predetermined region by image processing for an ultrasonic image, wherein a position of the predetermined region depends on a position of a boundary between the blood flow region and the tissue region; and
correction processing including (a) generating a smoothed Doppler image by smoothing at least the predetermined region of the original Doppler image, (b) generating a first weighted image by weighting at least the predetermined region of the original Doppler image with a first weighting factor and generates a second weighted image by weighting at least the predetermined region of the smoothed Doppler image with a second weighting factor, and (c) generating a blend image by blending the first weighted image and the second weighted image.

21. The ultrasonic image processing method according to claim 20,
wherein the first weighting factor and the second weighting factor for each image element in the predetermined region depend on a position of the each image element in the predetermined region.

22. The ultrasonic image processing method according to claim 20,
wherein the first weighting factor and the second weighting factor for each image element in the predetermined region depend on a speed of a blood flow or a speed of a tissue at the each image element.

23. The ultrasonic image processing method according to claim 20,
wherein the correction processing further varies the blending in response to a distance from the tissue region to the predetermined region.

24. The ultrasonic image processing method according to claim 20, wherein the correction processing detects the blood flow region, and image correction processing using only the second weighted image is executed in a region other than the blood flow region.

25. The ultrasonic image processing method according to claim 20, further comprising:
- determining a writing direction of data of the original Doppler image into a memory in response to size and shape of the predetermined region to which an ultrasonic wave is transmitted; and
- writing the data into the memory according to the determined direction,
- wherein the correction processing is executed by using the data written into the memory according to the determined direction.

26. The ultrasonic image processing method according to claim 20,
- wherein the original Doppler image and ultrasonic image data are three-dimensional image data.

* * * * *